United States Patent [19]

Hooven

[11] Patent Number: 4,769,002
[45] Date of Patent: Sep. 6, 1988

[54] INTERCRANIAL PRESSURE REGULATOR VALVE

[75] Inventor: Michael D. Hooven, Miami, Fla.

[73] Assignee: Cordis Corporation, Miami, Fla.

[21] Appl. No.: 837,333

[22] Filed: Feb. 28, 1986

Related U.S. Application Data

[63] Continuation of Ser. No. 467,326, Feb. 17, 1983, abandoned.

[51] Int. Cl.$^4$ ............................................. A61M 27/00
[52] U.S. Cl. ........................................ 604/9; 604/247;
251/65; 137/508; 137/539
[58] Field of Search ................... 604/9, 8, 248, 247;
251/65; 137/508, 570, 539; 128/748

[56] References Cited

U.S. PATENT DOCUMENTS

| 1,139,455 | 5/1915 | Gase . | |
|---|---|---|---|
| 2,879,783 | 11/1956 | Tadlin | 137/163 |
| 3,270,771 | 9/1966 | Morgan et al. . | |
| 3,768,508 | 10/1973 | Schulte | 604/9 |
| 3,769,982 | 11/1973 | Schulte | 604/9 |
| 3,804,113 | 4/1974 | Garcea . | |
| 3,886,948 | 6/1975 | Hakim | 604/9 |
| 3,901,245 | 8/1975 | Spitz et al. | 604/9 |
| 3,999,553 | 12/1976 | Spitz et al. | 604/9 |
| 4,106,510 | 8/1978 | Hakim et al. | 604/9 |
| 4,156,422 | 5/1979 | Hildebrandt et al. | 128/748 |
| 4,246,930 | 1/1981 | Bishop et al. | 137/502 |

FOREIGN PATENT DOCUMENTS 68509 8/1951 Netherlands .

Primary Examiner—Stephen C. Pellegrino
Attorney, Agent, or Firm—Lockwood, Alex, FitzGibbon & Cummings

[57] ABSTRACT

An intercranial pressure regulator valve adapted particularly for the treatment of hydrocephalus and the draining of cerebrospinal fluid (CSF) from a ventricle in the brain to another location in the patient's body includes a movable, flexible diaphragm having first and second surfaces of substantial area which are contacted by the fluid which is being drained and the fluid in the area to which the CSF is to be drained, respectively. A valve seat on the diaphragm is movable therewith and the valve seat includes a passage for the flow of the fluid which is being drained through the diaphragm. A ball closure valve is positioned on the cephalad side of the diaphragm. When the pressure differential on both surfaces of the diaphragm is low, the valve seat flexes into engagement with the ball closure valve to close the passage. When the pressure differential between these two surfaces increases, the diaphragm flexes in response to the increase such that the valve seat moves away from the ball closure valve to open the passage and drain the CSF from the ventricle to the other location in the body.

43 Claims, 1 Drawing Sheet

U.S. Patent    Sep. 6, 1988    4,769,002
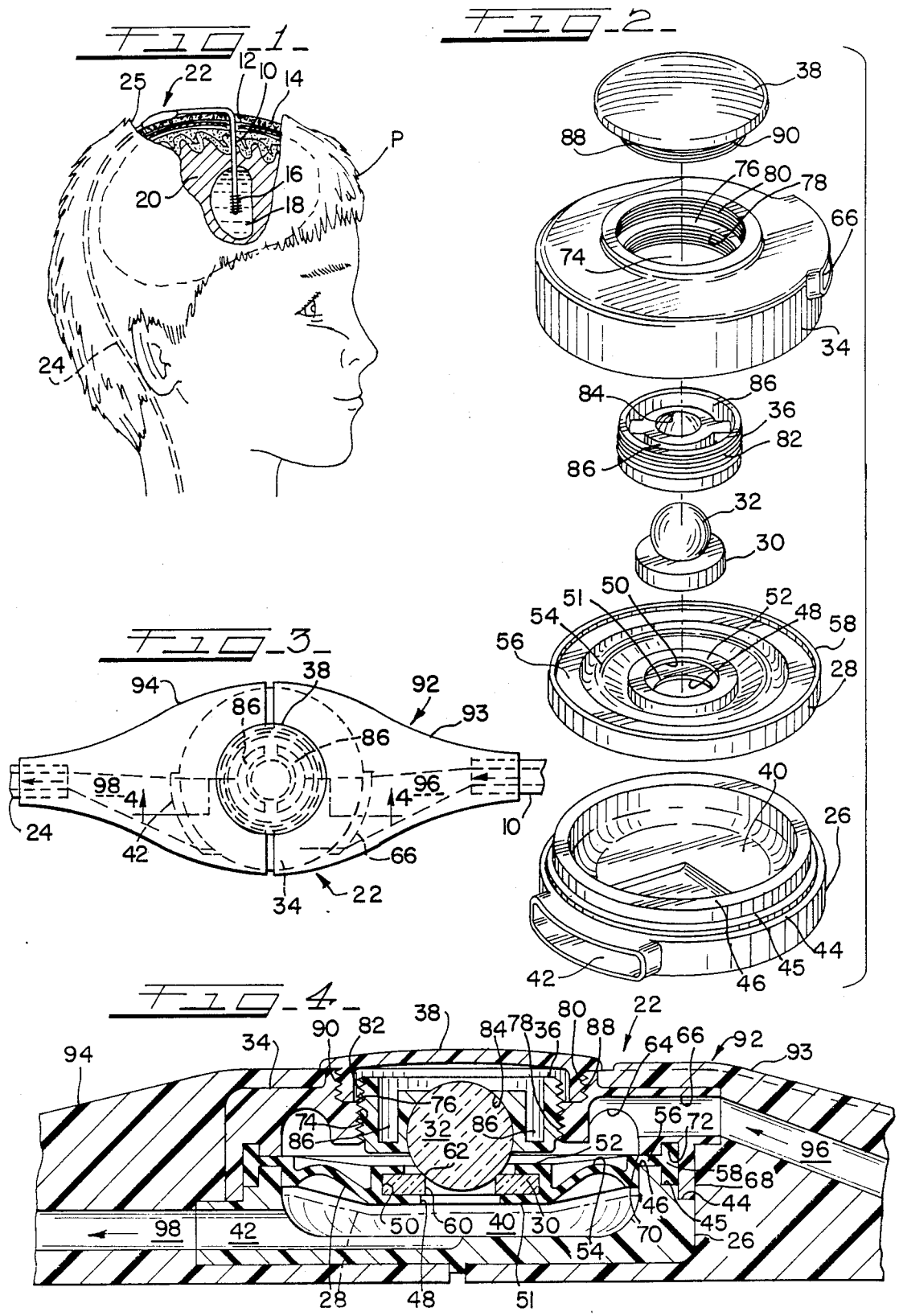

INTERCRANIAL PRESSURE REGULATOR VALVE

This application is a continuation of application Ser. No. 467,326, filed Feb. 17, 1983, now abandoned.

BACKGROUND AND SUMMARY OF THE INVENTION

The present invention relates to an intercranial pressure regulator valve and, more particularly, to a valve for and method of shunting excess cerebrospinal fluid (CSF) from a ventricle in the brain to another location in the patient's body when the pressure differential between the CSF and the other body fluid reaches a predetermined magnitude.

Hydrocephalus is a condition in which the brain is unable to relieve itself of CSF which collects in the ventricles of the brain. Such CSF, thereby, becomes excessive and results in abnormal ventricular size causing a number of adverse physiological effects including compression of the brain tissue, impairment of the blood flow in the brain tissue and of the brain's normal metabolism.

A variety of CSF pressure regulator valves and methods of controlling CSF pressure have been developed in the past which include various forms of check valves, servo valves or combinations thereof. Although these prior valves operate with some degree of success in the treatment of hydrocephalus, difficulty in the operation of such valves may be experienced due to the miniaturization of the valves and the relatively low pressures and volumes with which they must work.

An intercranial pressure regulator valve and method of draining body fluids in accordance with the principles of the present invention minimizes such difficulties in operation. In a valve and method of the present invention, performance is substantially improved in extremely small, miniaturized regulator valves, yet the valves are fully hydraulic in operation. In a regulator valve and method incorporating the principles of the present invention, the body fluid pressures may be accurately regulated and the valve is extremely responsive to minute changes in the pressure of the fluids. In a valve and method incorporating the principles of the present invention, the body fluids act on surfaces of substantial area and on both sides of a movable member or diaphragm so that the valve and method of the present invention is responsive to substantially smaller pressure differentials than the valves and methods of the prior art. In a valve and method of the present invention, the pressures at which response occurs may be rapidly and easily adjusted without interfering with the operation of the valve. In a valve and method incorporating the principles of the present invention, springs may be eliminated and a diaphragm or other movable member which is responsive to pressure variations may, instead, be employed, thereby reducing the number of parts, the possibility of malfunction and other disadvantages which may be associated with such springs.

In one principal aspect of the present invention, a valve for the passage of body fluids from one location in the body to another and the regulation of the pressure of such fluids comprises movable means having first and second surfaces of substantial area thereon. First coupling means communicates the area of the first surface with the fluid from the one location and a second coupling communicates the area of the second surface with the other location. Valve seat means on the movable means is movable therewith and includes a passage for the flow of the fluid from the first to the second surfaces. Valve closure means is positioned on the side of the movable means adjacent the first surface. The valve closure means is engaged by the movable valve seat means to close the passage in response to a first lower pressure differential of the fluid acting on the first and second surfaces, and the movable means and its valve seat means is movable away from the valve closure means to open the passage in response to a second higher pressure differential of the fluid acting on the first and second surfaces.

In another principle aspect of the present invention, the aforementioned movable means is a flexible diaphragm.

In still another principal aspect of the present invention, the aforementioned passage extends through the movable means or diaphragm.

In still another principal aspect of the present invention, the aforementioned valve closure means includes means for stationarily mounting the valve closure means such that the valve seat means moves relative to the valve closure means.

In still another principal aspect of the present invention, the valve closure means includes adjustment means for adjusting the force by which the valve seat means engages the valve closure means.

In still another principal aspect of the present invention, the aforementioned valves drain cerebrospinal fluid (CSF) and the first coupling means includes a catheter for communicating with the tissue in the body from which the CSF is to be drained.

In still another principal aspect of the present invention, the aforementioned valve closure means comprises a substantially spherical ball which is engageable by the valve seat means.

In still another principal aspect of the present invention, a method of draining body fluids from one location in the body to another location to regulate the pressure of the fluid includes communicating the fluids at the one location with a first surface of substantial area on a movable member. A passage which communicates the first surface with a second surface also of substantial area on the movable member is closed when the pressure differential between the surfaces is at a first lower pressure differential by moving the movable member and a valve seat mounted thereon relative to and into engagement with a substantially stationary valve closure means. The passage is opened to communicate the first surface with the second surface when the pressure differential between the surfaces is at a second higher pressure differential and in response to the second higher differential by moving the movable valve closure means to drain the fluids from the one location to the other location.

In still another principle aspect of the present invention, in the last mentioned method, the movable member is a flexible diaphragm and the pressure differentials cause the diaphragm to flex to result in the movement of the movable member and valve seat.

In still another principal aspect of the present invention, the aforementioned methods include adjusting the valve closure means to adjust the force by which the valve seat engages the valve closure means to alter the second higher pressure differential.

In still another principal aspect of the present invention, in the aforementioned methods, the fluid is CSF.

These and other objects, features and advantages of the present invention will be clearly understood through a consideration of the following detailed description.

BRIEF DESCRIPTION OF THE DRAWINGS

In the course of this description, reference will frequently be made to the attached drawing in which:

FIG. 1 is illustrative of a hydrocephalus system in which the preferred embodiment of intercranial pressure regulator valve of the present invention may be incorporated and the preferred method of the present invention may be practiced;

FIG. 2 is an enlarged, exploded view of a preferred embodiment of valve incorporating the principles of the present invention;

FIG. 3 is a reduced, plan view of the assembled valve shown in FIG. 2 as incorporated in the hydrocephalus treatment system shown in FIG. 1; and FIG. 4 is an enlarged, cross-sectioned, partially broken, side elevational view of the valve as viewed substantially along line 4—4 in FIG. 3.

DESCRIPTION OF THE PREFERRED EMBODIMENT

In FIG. 1 a hydrocephalus system incorporating the principles of the present invention is illustrated. The system shown includes a ventricle catheter 10 which is inserted through an opening 12 which has been formed in the skull 14 of the patient P who is to undergo the hydrocephalus treatment. The catheter 10 is preferably radiopague. The distal end 16 of the ventricular catheter 10 is positioned in a ventricle 18 in the patient's brain tissue 20 in which the CSF accumulates. The other end of the catheter 10 is coupled to the intercranial pressure regulator valve 22 of the present invention, as shown in FIG. 1, and a drain catheter 24 is coupled to the valve 22 to receive the discharge from the valve to drain the CSF discharge to another location in the patient's body, such as the right atrium of the patient's heart (not shown). The valve 22, the portion of the ventricle catheter 10 exterior to the skull 14, and the drain catheter 24 are preferably located between the patient's skull 14 and scalp 25, as shown in FIG. 1.

The details of the valve 22 are best shown in FIGS. 2-4. As shown in FIG. 2, the preferred embodiment of pressure regulator valve incorporating the principles of the present invention includes a valve casing bottom 26, a flexible diaphragm 28, a valve seat 30 and valve closure ball 32, a valve casing top 34, a threaded screw member 36, and a casing closure cap 38. The casing bottom 26, casing top 34, screw member 36 and closure cap 38 are formed of a suitable durable, biologically compatible material, such as thermoplastic polymers of polyethersulfone or polycarbonates.

The valve casing bottom 26 comprises a substantially cup shaped member which defines, as shown in FIG. 4, a fluid discharge chamber 40 having a discharge port 42 of preferably elongate cross-section as shown in FIG. 2. The upper rim of the casing bottom 26 is formed with a plurality of stepped raised shoulders 44, 45 and 46.

The diaphragm 28 comprises a preferably substantially circular, flexible movable disc having a fluid flow passage 48 adjacent its center. An annular groove 50 is formed in the diaphragm adjacent the flow passage 48 to receive and hold the valve seat 30 as shown in FIG. 4. The groove 50 is defined by a lower flange 51 and an upper flange 52, the upper flange 52 being preferably somewhat shorter than the lower flange 51 to accommodate unrestricted movement of the diaphragm and valve seat 30 relative to the valve closure ball 32 during operation of the valve. The lower flange 51 is surrounded by an annular disc portion 54 which is preferably convoluted when installed in the casing, as shown in FIG. 4. The convolution provides increased flexibility of the diaphragm and stability against cocking during operation. A horizontal annular flange 56 surrounds the annular disc portion 54. The annular flange 56 is encircled by a generally vertical annular flange 58 to complete the diaphragm construction. The diaphragm 28 may be formed of any durable, flexible, biologically compatible material, such as Silastic rubber.

The valve seat 30 is preferably circular, as shown in FIGS. 2 and 4, and includes an opening 60 through its center to provide for the passage of fluid through the diaphragm. A suitable shoulder 62 is formed at the top of the opening 60 in valve seat 30 to engage the valve closure ball 32 to form a seal with the ball 32 to block passage of the fluid through the opening 60.

The valve closure ball 32 is positioned on the cephalad side of the diaphragm and is preferably substantially spherical in shape, as shown in FIGS. 2 and 4, although it will be understood that other shapes may be satisfactorily employed in the present invention. As shown in FIG. 4, valve closure ball 32 is solid, although it may be hollow, if desired.

Both the valve seat 30 and valve closure ball 32 are also formed of a durable, yet biologically compatible material. By way of example, sapphire may be used as a material to form the valve seat and ball.

The valve casing top 34 also comprises a substantially cup shaped member which defines, as shown in FIG. 4, an inlet chamber 64 and an inlet port 66, the latter of which is also of elongate oblong cross-section, as best seen in FIG. 2. The casing top 34 includes, as best shown in FIG. 4, a pair of downwardly extending annular flanges 68 and 70 with flange 68 being somewhat longer than flange 70. Flanges 68 and 70 are spaced from each other to define a groove 72 therebetween. The diameter and width of flange 70 are preferably substantially equal to the diameter and width of shoulder 46 on the casing bottom 26 and overlies that shoulder when the casing is assembled, as shown in FIG. 4. The diameter and width of groove 72 are substantially equal to the diameter and width of shoulder 45 on the casing bottom and overlies that shoulder when the casing is assembled, as shown in FIG. 4. The diameter and width of flange 68 are substantially equal to the diameter and width of shoulder 44 on the casing bottom and overlies that shoulder when the casing is assembled. The vertical annular flange 58 of the diaphragm 28 is clamped between the groove 72 and shoulder 45 and the horizontal annular flange 56 of the diaphragm is clamped between the flange 70 and shoulder 46 when the valve casing is assembled, as shown in FIG. 4. The valve casings and diaphragm, thereby, fit snugly together when assembled and they are all secured together by suitable means such as solvent, adhesive or ultrasonic bonding.

An opening 74 extends through the top of the top valve casing 34. The opening is preferably stepped at 76 and the wall of the opening is threaded with two sets of threads 78 and 80.

The screw member 36 contains external threads 82 on its outside surface which are adapted to be threaded into the threads 78 in the opening 74 of the casing top. The ball 32 is attached in a recess 84 in the screw member 36 by suitable means, such as insert molding. The ball 32 is, therefore, stationarily mounted to the screw member. A pair of arcuate slots 86 are also formed in the screw member, as shown in FIG. 2, to receive a suitable tool for adjusting the extent to which the screw member is threaded into the casing top.

The closure cap 38 includes a downwardly extending annular flange 88 which contains threads 90 on its external surface so that the cap may be threaded onto the threads 80 for closure of the opening 74 in the casing top 34.

Once the lower and upper valve casings 26 and 34 the diaphragm 28, the valve seat 30, the ball 32 and the screw member 36 have been assembled together, a flexible outer housing is assembled over the valve casing by sliding the outer housing over the valve casing. This flexible outer housing 92 is preferably formed by a pair of housing half members 93 and 94, as shown in FIGS. 3 and 4. Housing half member 93 includes a tapering inlet antichamber 96 which, at its wider end, communicates with the inlet port 66 and at the other narrower end with the ventricular catheter 10. The other housing half member 94 also includes a tapered discharge antichamber 98 which, at its wider end, communicates with the discharge port 42 and at the other narrower end with the drain catheter 24. The outer housing 92 is formed of a flexible, biologically compatible material, such as Silastic rubber.

The closure cap 38 is preferably exposed through the housing 92, as shown in FIGS. 3 and 4, to allow adjustment of the screw member 36 and its ball 32 during the assembly of the valve system.

Although the operation of the intercranial pressure regulator valve and method of the present invention should be clear from the foregoing description, a brief description of a preferred operation and method of hydrocephalus treatment will be described.

The CSF in the ventricle 18 which is to be drained communicates with the valve via the ventricular catheter 10, the inlet antichamber 96 in the housing half member 93, the inlet port 66 and the inlet chamber 64. Thereby, the pressure of this CSF will act upon substantially the entire upper surface of the diaphragm 28 which is of substantial area as may be seen in FIG. 4. So long as the pressure of the fluid on the discharge side of the valve which is also acting upon the entire lower surface of the diaphragm 28 is substantially equal to the pressure of the CSF acting upon the upper surface of the diaphragm, the resilient nature of the diaphragm will cause it to flex upwardly, as viewed in FIG. 4, and cause the valve seat 30 to engage the stationary valve closure ball 32 to close the passages 48 and 60 through the diaphragm and valve seat and prevent flow of the fluid through these passages.

When a pressure increase occurs in the CSF in the ventricle, this increased pressure will be transmitted to the upper surface area of the diaphragm 28. When the pressure differential increases between the upper surface area of the diaphragm and the fluid in the discharge chamber 40 which exerts its pressure against the bottom surface area of the diaphragm, the diaphragm will begin to flex downwardly, as shown by the dot and dash lines in FIG. 4, in response to this increased differential in pressure. Such flexing will cause the valve seat 30 to move away from the stationary valve closure ball 32 and allow CSF to pass between the upper surface of the diaphragm from chamber 64 through the passages 48 and 60 to the discharge chamber 40 and the lower surface of the diaphragm. This fluid will be discharged through the discharge port 42, discharge antichamber 98 and discharge catheter 24. The discharge of CSF through passages 48 and 60 will continue until the pressure differential between the upper and lower surfaces of the diaphragm returns to a predetermined low differential causing the diaphragm to again flex upwardly until the valve seat 30 engages the valve closure ball 32 to close the passages 48 and 60.

The pressure differential at which the valve opens may be adjusted as necessary for the patient. This adjustment may be readily accomplished by threading up or down the screw member 36 to adjust the force by which the spherical ball 32 bears against the valve seat. If the ball 32 is moved downwardly, it will preflex the diaphragm downwardly somewhat resulting in a higher pressure differential which must be reached before the valve seat 30 begins to move away from the ball 32. The converse is true if the ball is threaded upwardly, as viewed in FIG. 4.

From the foregoing description it will be seen that the valve and method of the present invention are extremely responsive to very low changes in pressure of the CSF. This responsiveness is a result of the fact that the fluid pressures which act upon the surfaces of the diaphragm are exerted over substantially the entire areas of the upper and lower surfaces of the diaphragm. Thus, very small changes in pressure differential are capable of actuating the valve. By way of example, the pressure regulator valve described herein is capable of accurate operation at CSF pressure differentials of between 0-200 millimeters of water.

Moreover, extreme sensitivity of response may be realized in pressure regulator valves of very small size, for example valves which may be only one-fourth inch in thickness and three quarter inch in diameter.

It will also be seen that the valve incorporating the principles of the present invention may be easily and rapidly adjusted to conform with the pressure differential requirements of a given patient. Such adjustment may be accomplished without interfering in any manner with the valve operation itself.

Although the present invention has been shown in a system for draining a ventricle in the brain tissue of a patient, it will be understood that the valve and method of the present invention may be readily employed in the control and regulation of the pressure of various other body fluids from and to various other body cavities of the patient. By way of example, the present invention may be employed in the draining and regulation of spinal or other fluids of the patient.

It will also be understood that the embodiment of the present invention which has been described is merely illustrative of one of the applications of the principles of the present invention. Numerous modifications may be made by those skilled in the art without departing from the true spirit and scope of the invention.

What is claimed is:

1. A valve for regulating the flow of fluid from one location in the body to another location, comprising:
 a bio-compatible housing;
 a flexible bio-compatible diaphragm dividing theinterior of said housing into first and second interior chambers;
 inlet port means for establishing fluid communication between said first interior chamber and the one location;

output port means for establishing fluid communication between said second interior chamber and the other locatin;

a bio-compatible valve seat member carried on said diaphragm for movement therewith, said valve seat defining a fluid passageway opening from said first interior chamber to said second interior chamber and having a first valving surface concentrically oriented with respect to the axis of said fluid passageway, said valve seat and diaphragm having a static position within said housing in the absence of a pressure differential between said chambers;

means comprising a bio-compatible valve closure member in said first interior chamber axially aligned with said fluid passageway, said valve closure member having a second valving surface concentrically oriented with respect to the axis of said fluid passageway, said second valving surface coacting with said first valving surface to form a constricting portion within said passageway between said first and second chambers whcn valve seat is in said static position to at least partially close said fluid passageway; and said diaphragm being displaceable from said static position in a direction to move said valve seat member along said axis of said fluidpassageway and away from said valve closure member in response to a predetermined minimum threshold pressure differential between said first interior chamber and said second interior chamber to at least partially open said fluid passageway to increase fluid flow between said first and second interior chambers to maintain said pressure differential.

2. A flow regulating valve as defined in claim 1, wherein said first valving surface engages said second valving surface to close said fluid passageway when said valve seat member is in said static position to prevent fluid flow between said first and second chambers when the pressure differential between said chambers is less than said threshold level.

3. A flow regulating valve as defined in claim 2 wherein said first valving surface is biased into engagement with said second valving surface by said diaphragm when said valve seat is in said static position to increase said threshold pressure differential at which flow occurs between said first and second interior chambers.

4. A flow regulating valve as defined in claim 1, wherein said valve seat and said valve closure member are each formed of a hard substantially non-deformable material.

5. A flow regulating valve as defined in claim 4 wherein said hard substantially non-deformable material is saphire.

6. A valve for regulating the flow of fluid from one location in the body to another location, comprising:

a housing;

a flexible bio-compatible diaphragm dividing the interior of said housing into first and second interior chamber;

inlet port means for establishing fluid communication between said first interior chamber and the one location;

outlet port means for establishing fluid communication between said second interior chamber and the other location;

a bio-compatible valve seat carried on said diaphragm for movement therewith, said valve seat defining a fluid passageway opening from said first interior chamber to said second interior chamber, and said valve seat and diaphragm having a static position within said housing in the absence of a pressure differential between said chambers;

means comprising a bio-compatible valve closure member in said first interior chamber for coacting with said valve seat when said valve seat is in said static position to at least partially close said fluid passageway;

said diaphragm being displaceable from said static position in a direction away from said valve closure member in response to a predetermined minimum threshold pressure differential between said first interior chamber and said second interior chamber to at least partially open said fluid passageway to increase fluid flow between said first and second interior chambers; and adjusting means for adjusting the position of said valve closure member within said first chamber to vary said threshold pressure differential at which said increased flow occurs.

7. A flow regulating valve as defined in claim 6 wherein said valve closure means engage said valve seat to close said fluid passageway when said valve seat is in said static position to prevent fluid flow between said first and second chambers when the pressure differential between said chambers is less than said threshold level.

8. A flow regulating valve as defined in claim 7 wherein said valve seat is biased into engagement with said valve closure means by said diaphragm when said valve seat is in said static position to increse the threshold pressure differential at which flow occurs between said first and second interior chambers.

9. A flow regulating valve as defined in claim 6 wherein said valve seat is carried at the center of said diaphragm and said valve closure member is mounted in said first interior chamber in axial alignment with said passageway.

10. A flow regulating valve as defined in claim 9 wherein said adjusting means include means for adjusting the position of said valve closure member within said first chamber along said axis.

11. A flow regulating valve as defined in claim 6 wherein said adjusting means include a user accessable actuator member for actuating said adjustment means from the exterior of said housing.

12. A flow regulating valve as defined in claim 6 wherein said adjusting means include an adjustment member mounted in said first interior chamber for movement toward and away from said diaphragm and said valve closure member is mounted on said member.

13. A flow regulating valve as defined in claim 12 wherein said adjustment member comprises a screw member threadably engaged to said housing and rotatable from the exterior thereof.

14. A flow regulating valve as defined in claim 13 wherein said screw member displaced said valve closure means toward said diaphragm in response to rotation of said screw member in one direction and displaces said valve closure means in a direction away from said diaphragm in response to rotation of said screw member in the opposite direction.

15. A flow regulating valve as defined in claim 6, wherein said valve seat and said valve closure member are each formed of a hard substantially non-deformable material.

16. A flow regulating valve as defined in claim 15 wherein said hard substantially non-deformable material is saphire.

17. A flow regulating valve as defined in claim 6 wherein said fluid passageway is generally circular in cross-section and said valve closure member comprises a substantially spherical surface dimensioned for liquid sealing engagement therewith.

18. A valve for regulating the flow of fluid from one location in the body to another location, comprising:
  a housing;
  a flexible bio-compatible diaphragm dividing the interior of said housing into first and second interior chambers;
  inlet port means for establishing fluid communication between said first interior chamber and the one location;
  outlet port means for establishing fluid communication between said second interior chamber and the other location;
  a bio-compatible valve seat carried on said diaphragm for movement therewith, said valve seat defining a fluid passageway opening from said first interior chamber to said second interior chamber, and said valve seat and diaphragm having a static position within said housing in the absence of a pressure differential between said chambers;
  means including a bio-compatible valve closure member in said first interior chamber for engaging said valve seat when said valve seat is in said static position to close said fluid passageway, said diaphragm being displaced by said closure member from an unstressed position to bias said valve seat into engagement with said valve closure member;
  said diaphragm being displaceable from said static position in a direction away from said valve closure member in response to a predetermined minimum threshold pressure differential between said first interior chamber and said second interior chamber overcoming said bias of said diaphragm to at least partially open said fluid passageway to increase fluid flow between said first and second interior chambers; and
  adjusting means for adjusting the position of said valve closure member within said first chamber to vary said threshold differential at which said increased flow occurs.

19. A flow regulating valve as defined in claim 18 wherein said valve seat is carried at the center of said diaphragm and said valve closure member is mounted in said first interior chamber in axial alignment with said passageway.

20. A flow regulating valve as defined in claim 19 wherein said adjusting means include means for adjusting the position of said valve closure member within said first chamber along said axis.

21. A flow regulating valve as defined in claim 18 wherein said adjusting means include a user accessible actuator member for actuating said adjustment means from the exterior of said housing.

22. A flow regulating valve as defined in claim 18 wherein said adjusting means include an adjustment member mounted in said first interior chamber for movement toward and away from said diaphragm and said valve closure member is mounted on said member.

23. A flow regulating valve as defined in claim 22 wherein said adjustment member comprises a screw member threadably engaged to said housing and rotatable from the exterior thereof.

24. A flow regulating valve as defined in claim 18, wherein said valve seat and said valve closure member are each formed of a hard substantially non-deformable material.

25. A flow regulating valve as defined in claim 24 wherein said hard substantially non-deformable material is saphire.

26. A flow regulating valve as defined in claim 18 wherein said fluid passageway is generally circular in cross-section and said valve closure member comprises a substantially spherical surface dimensioned for liquid sealing engagement therewith.

27. A method of draining body fluids from one location in the body to another location to regulate the pressure of the fluids, comprising:
  communicating the fluids at said one location with a first location of substantial area on a movable member;
  closing a passage which communicates said first surface with a second surface of substantial area on the movable member when the differential in pressure between said surfaces is at a first lower pressure differential by moving said movable member and a valve seat mounted thereon relative to and into engagement with a substantially stationary valve closure means;
  opening said passage to communicate said first surface with said second surface with the pressure differential between said surfaces is at a second higher pressure differential by moving said movable member and said valve seat relative to and apart from said stationary valve closure means to drain the fluids from said one location to said another location; and
  adjusting said valve closure means to adjust the force by which said valve seat engages said valve closure means to alter said second higher pressure differential.

28. A method of drawing body fluids as defined in claim 2 wherein said fluid is cerebrospinal fluid.

29. A surgically-implantable shunt valve for venting cerebrospinal fluid in the treatment of hydrocephalus and for shunting other body fluids, said valve comprising
  a housing constructed of a surgically-implantable, non-metallic material,
  a diaphragm support consisting of a single flexible diaphragm mounted within said housing,
  a plate mounted on said flexible diaphragm, said plate being provided with a circular aperture and said diaphragm having an opening aligned with said aperture,
  said diaphragm being generally coplanar with said plate,
  said diaphragm and plate dividing said housing into an inlet and an outlet chamber that communicate through said aperture,
  said inlet and outlet chambers being generally free of blind cavities so as to inhibit collection of debris,
  a valve element of diameter larger than said aperture, said valve element residing on the inlet side of said aperture,
  means for biasing said valve element against the circular periphery of said aperture so as to keep said aperture closed until the cerebrospinal fluid pressure in said inlet chamber exceeds a preselected popping pressure and so as to open said aperture when said popping pressure is exceeded so as to vent cerebrospinal fluid through said aperture into said outlet chamber, said popping pressure being on the order of cerebrospinal fluid pressures (i.e., less than 300 mm $H_2O$,)

said housing including inlet and outlet ports communicating with said inlet and outlet chambers respectively for connecting said inlet and outlet chambers to external catheters or other fluid conduits, and screw means for making external adjustments to said preselected popping pressure.

30. The shunt valve of claim 29 wherein said screw means includes means for making adjustments to the bias of said valve element against said circular periphery of said aperture.

31. The shunt valve of claim 30 wherein said screw means comprises a screw mounted in said housing.

32. The shunt valve of claim 31 wherein one end of said screw is exposed outside of said housing to provide for external adjustment.

33. The shunt valve of claim 32 wherein said exposed end is adapted to be adjusted by an instrument piercing the skin to make said adjustments.

34. The shunt valve of claim 29 wherein there is further provided valve element movement means for moving said ball in a direction normal to said plate and wherein said screw means includes means cooperating with said valve element movement means for moving said valve element by means of said external adjustments.

35. The shunt valve of claim 34 wherein said screw extends into said inlet chamber.

36. The shunt valve of claim 29 wherein said valve element is adhesively secured to said housing or other element of said valve.

37. The shunt valve of claim 36 wherein said ball is secured so that absent an adjustment of said screw means all movement of said valve element is prevented.

38. The shunt valve of claim 29 wherein said housing comprises two halves joined at mating faces and the periphery of said diaphragm is clamped between said two halves in the vicinity of said mating faces.

39. The shunt valve of claim 29 wherein said diaphragm and housing are generally circular in shape when viewed along a direction normal to said plate and aperture.

40. The shunt valve of claim 39 wherein said plate is circular and is mounted at the center of said circular diaphragm.

41. The shunt valve of claim 40 wherein said diaphragm is silicone rubber, said plate is stainless steel or sapphire, said valve element is a highly-polished, hard material such as sapphire, and said housing is injection molded using a surgically-implantable plastic such as polyethersulfone.

42. The shunt valve of claim 29 wherein the thickness of said plate is less than half the diameter of said valve element.

43. The shunt valve of claim 29 wherein said valve element is a spherical ball and wherein said screw means comprises a ball support means for stopping travel of said ball but not said plate, thereby causing said valve to open when said popping pressure is reached.

* * * * *